US011189372B2

(12) United States Patent
Poirier et al.

(10) Patent No.: US 11,189,372 B2
(45) Date of Patent: Nov. 30, 2021

(54) VERIFICATION SYSTEM FOR MEDICATION PACKAGING AND METHOD

(71) Applicant: RX-V INC., St-Laurent (CA)

(72) Inventors: Frederic Poirier, Boucherville (CA); Johnny Pietraroia, Mirabel (CA); Kim Bourbonnais, Boisbriand (CA)

(73) Assignee: RX-V INC., St-Laurent (CA)

( * ) Notice: Subject to any disclaimer, the term of this patent is extended or adjusted under 35 U.S.C. 154(b) by 0 days.

(21) Appl. No.: 16/575,912

(22) Filed: Sep. 19, 2019

(65) Prior Publication Data

US 2021/0090699 A1 Mar. 25, 2021

(51) Int. Cl.
| | |
|---|---|
| *G16H 20/10* | (2018.01) |
| *H04N 5/225* | (2006.01) |
| *G06K 9/20* | (2006.01) |
| *G06T 7/80* | (2017.01) |
| *G06T 7/90* | (2017.01) |

(52) U.S. Cl.
CPC ............ *G16H 20/10* (2018.01); *G06K 9/2036* (2013.01); *G06T 7/80* (2017.01); *G06T 7/90* (2017.01); *H04N 5/2256* (2013.01); *G06T 2207/10024* (2013.01); *G06T 2207/10152* (2013.01); *G06T 2207/30004* (2013.01); *G06T 2207/30242* (2013.01)

(58) Field of Classification Search
None
See application file for complete search history.

(56) References Cited

U.S. PATENT DOCUMENTS

| | | | | |
|---|---|---|---|---|
| 9,824,297 | B1* | 11/2017 | Guan | G06K 9/00335 |
| 2003/0169418 | A1* | 9/2003 | Fujii | G01N 21/95684 |
| | | | | 356/237.2 |
| 2006/0271237 | A1* | 11/2006 | Kim | B65B 61/24 |
| | | | | 700/226 |
| 2013/0342676 | A1* | 12/2013 | Amano | B65B 57/10 |
| | | | | 348/86 |
| 2015/0254821 | A1* | 9/2015 | Xu | G06K 9/00637 |
| | | | | 382/103 |
| 2016/0114925 | A1* | 4/2016 | Yuyama | B65B 57/16 |
| | | | | 382/141 |
| 2016/0210524 | A1* | 7/2016 | Hasegawa | G01N 21/85 |
| 2017/0305589 | A1* | 10/2017 | Yuyama | B65B 57/00 |
| 2019/0269576 | A1* | 9/2019 | Grosfils | G16H 20/13 |

FOREIGN PATENT DOCUMENTS

| | | |
|---|---|---|
| EP | 2902005 A1 | 8/2015 |
| GA | 2791818 C | 4/2014 |

* cited by examiner

*Primary Examiner* — Edemio Navas, Jr.
(74) *Attorney, Agent, or Firm* — Norton Rose Fulbright Canada LLP

(57) ABSTRACT

A system for verifying medication doses in a filled medication package comprises a camera(s), a contour light source (s), a set of relief light sources. A verification unit may be used for imaging a contour of the medication items, imaging a surface relief of the medication items, processing the images, confirming the content of the medication package relative to identification of a type of medication item and/or medication package using the processing of the images. An interface produces a verification output based on the confirmation by the verification unit.

21 Claims, 7 Drawing Sheets

VERIFICATION SYSTEM FOR MEDICATION PACKAGING AND METHOD

FIELD OF THE APPLICATION

The present application relates to medication packaging filled with medication as a function of personal prescriptions, and more particularly to the verification of the contents of medication packages versus personal prescriptions for example.

BACKGROUND OF THE ART

Prescribed medication packages are most often filled manually, from bulk containers. Due to the hundreds or thousands of types and dosages of medication items (e.g., tablets, pills, capsules) usually found in pharmacies, there exists an ongoing risk of human error in the preparation of prescribed medication packages. Such errors may include medication packages containing the incorrect tablets and/or doses. This may in some instances result in the manual verification of medication packaging vis àvis prescription to ensure the content is as prescribed. Considering that the medication containers are filled with a large quantity of medication items, and considering that improper doses and/or types of medication items can be harmful to individuals, great care is currently taken to ensure that medication trays are filled in accordance with a prescription. One verification step may be done by a pharmacy attendant, who visually inspects each compartment and compares the contents to a printed prescription. This is a time-costly process, and even requires in some regions the involvement of the pharmacist, because of regulations. Moreover, some types of medication items closely resemble one another such that a human eye may not even be capable of detecting an error.

SUMMARY OF THE APPLICATION

It is therefore an aim of the present application to provide a novel verification system for medication packaging.

Therefore, in accordance with a first embodiment, there is provided a system for verifying medication doses in a filled medication package, comprising a processing unit; and a non-transitory computer-readable memory communicatively coupled to the processing unit and comprising computer-readable program instructions executable by the processing unit for: obtaining an identification of a type of medication item and/or medication package containing the medication item, imaging a contour of the medication items by operating at least a first light source, imaging a surface relief of the medication items by operating a first set of lights differing from the first light source, processing the images, confirming the content of the medication package relative to identification of a type of medication item and/or medication package using the processing of the images, and outputting the confirmation of the content.

In accordance with another embodiment of the present disclosure, there is provided a system for verifying medication doses in a filled medication package, comprising at least one camera; at least one contour light source; a set of relief light sources; a verification unit including a processing unit and a non-transitory computer-readable memory communicatively coupled to the processing unit and comprising computer-readable program instructions executable by the processing unit for obtaining an identification of a type of medication item and/or medication package containing the medication item, imaging a contour of the medication items by operating the at least one contour light source, imaging a surface relief of the medication items by operating the set of relief light source differing from the contour light source, processing the images, confirming the content of the medication package relative to identification of a type of medication item and/or medication package using the processing of the images; and an interface for producing a verification output based on the confirmation by the verification unit.

DESCRIPTION OF THE PREFERRED EMBODIMENTS

Figure 1:
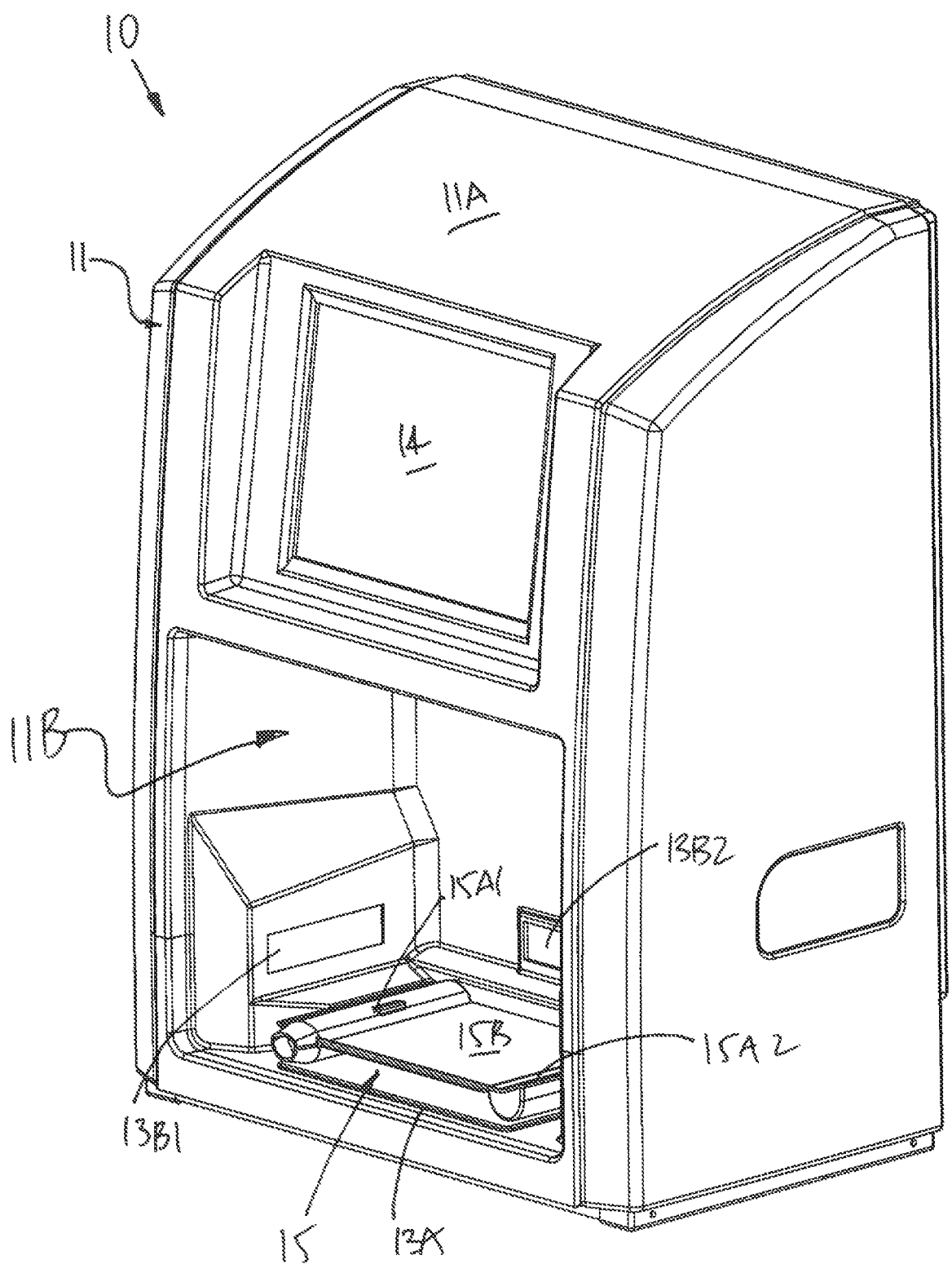
FIG. 1 is a perspective view of an exemplary verification system for medication packages in accordance with the present disclosure.
Figure 2:
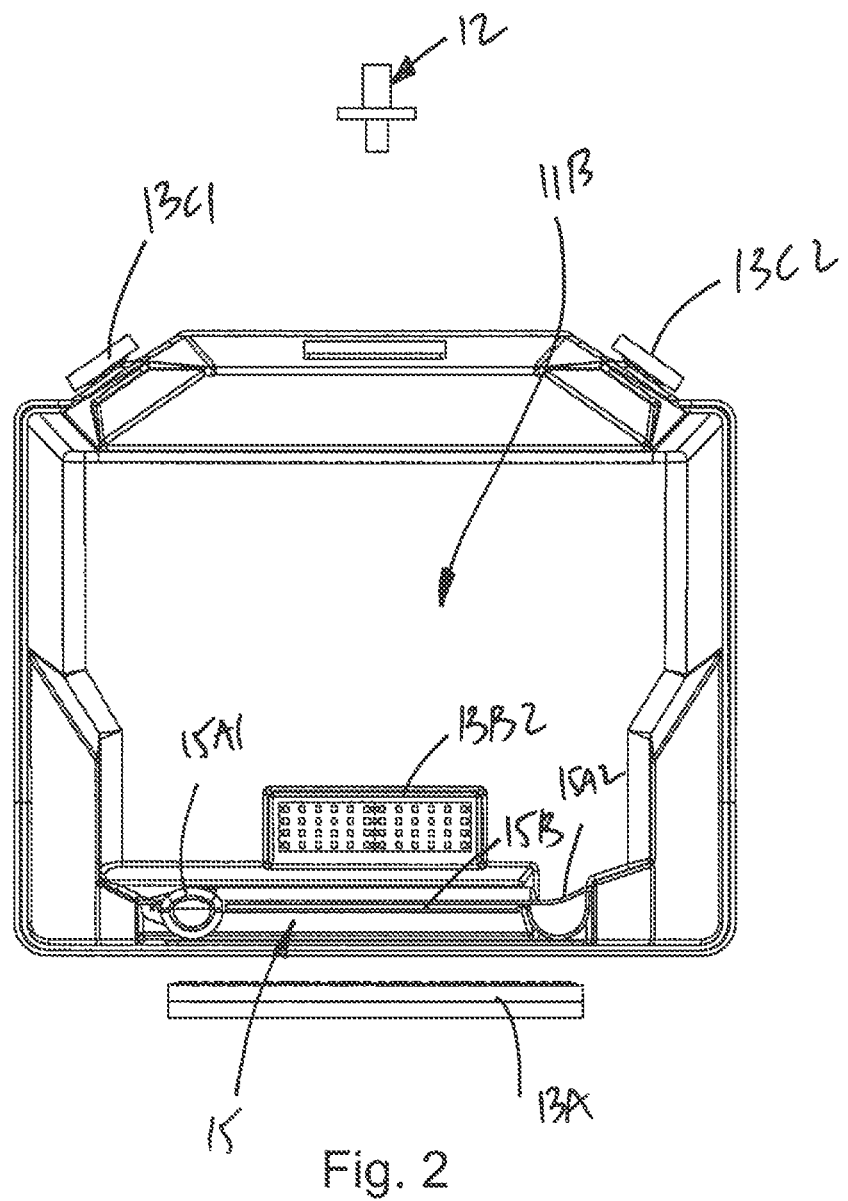
FIG. 2 is an elevation view of an imaging volume of the verification system of FIG. 1.
Figure 3:
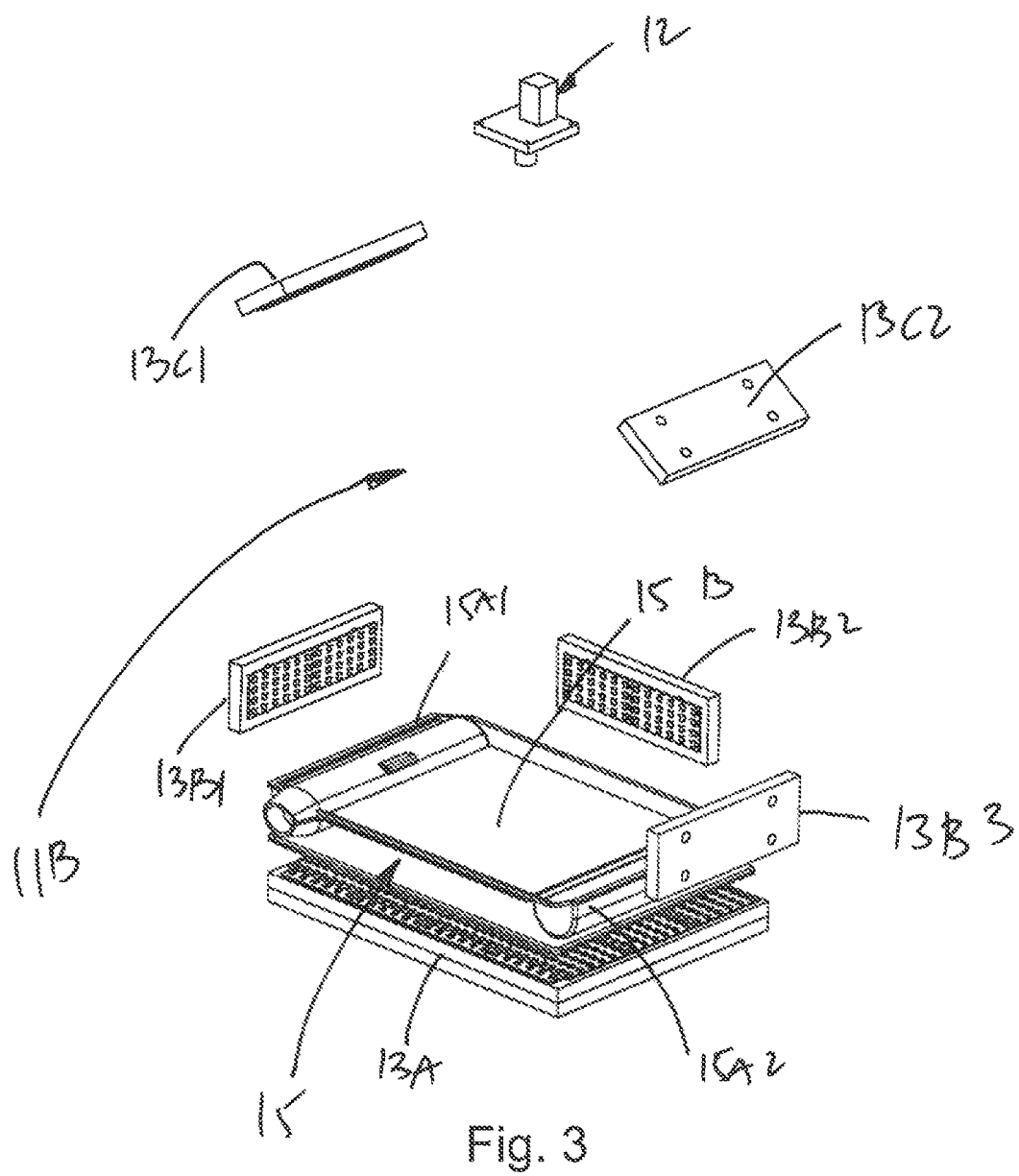
FIG. 3 is a perspective view of a camera, light sources, and tray of the verification system of FIG. 1.

Referring to FIGS. 1 to 5, a verification system for medication packages is generally shown at 10, with respect to a filled medication package A. The medication package A may be any type of package enclosing medication, such as medication trays, tubular containers, pill packs, blister card or pack, bulk container, PCI controlled dosage system, Pharmacard™, vials, or any other medication packaging. In an embodiment, the filled medication package A is filled with a single type of medication item (i.e., same dose of one type of medication, having a drug identification number (DIN)) and is tied to a patient prescription, also known as a patient posologic profile. For simplicity purposes, reference will be made to a medication package A or filled package A hereinafter, but the disclosure is intended to cover uses of the verification system 10 with any appropriate type of medication packages, provided the use is in accordance with the present disclosure. Moreover, reference is made hereafter to the filled package A as comprising medication items, with medication items generically referring to any geometrically defined medication doses (as opposed to liquids, powder), such as pills, tablets, capsules, hard gelatin capsules, etc.

The verification system 10 has a casing body or like structure 11, a camera(s) 12, light sources 13, an interface unit 14, a tray 15, and/or a verification unit 20.

The structure 11 is the structural component of the system 10, in that it holds and shields the various components.

The camera 12 may optionally obtain images of the medication package A, such as its label, barcode, etc, and obtains images of the medication items in the medication package A.

The light sources 13 produce different lighting schemes to vary the image parameters of the images obtained by the camera 12.

The interface unit 14 outputs a verification report in any appropriate format, as will be described hereinafter, in addition to guiding an operation of the verification system 10.

The tray 15 is provided to support the medication items during the imaging.

The verification unit 20 includes the operation software that processes the images and compares them to data related to a prescription, and performs a verification. The verification unit 20 may also guide an operator through the medication verification procedure via the interface unit 14.

The structure 11 may be in the form of or may include a casing body defining or contributing to the structure of the verification system 10. Accordingly, the casing body encloses and/or supports the components of the verification system 10 described herein. As some of the components of the verification system 10 are fragile, calibrated, in a specific location, etc, the casing body 11 protects the integrity of the verification system 10 and ensures its proper operation. The verification system 10 may be a self-contained system, with the casing body 11 being wired for powering, and for network communication, though the verification system 10 may be equipped with wireless capacity.

As observed from FIG. 1, the casing body 11 may include outer shell body 11A incorporating structural components like a frame or frame members. In an embodiment, the outer shell body 11A may have structural integrity to support the components of the verification system 10 in the manner described herein, and/or may conceal structural members such as frame members. The outer shell body 11A may be made of polymers, metals, composites, and may have esthetic features. In another embodiment, the outer shell body 11A may be absent, with a frame being used without shell components. Other embodiments are considered as well. For simplicity, reference will be made to the casing body 11 herein, though the structure 11 may be without such body. The body 11 may also prevent tampering with some functional components of the verification system 10.

The casing body 11 or structure 11 defines an imaging volume 11B in which imaging is performed. In an embodiment, the camera 12, the light sources 13 and the tray 15 (if present) have exposure in the imaging volume 11B. In an embodiment, the camera 12 and the light sources 13 are mounted to the walls of the outer shell body 11A and are fixed in position. The tray 15 may for example be seated in a bottom of the imaging volume 11B, such as by being on a bottom surface of the casing body 11 or on a table or like surface supporting the verification system 10. The imaging volume 11B defines a generally confined space, accessible from a front end of the casing body 11.

Consequently, the imaging volume 11B may be partially isolated from environmental and/or incidental light. In an embodiment, though not shown, a door or trap may be present to access the imaging volume 11B, and filter out environmental and/or incidental light. Moreover, surfaces surrounding the imaging volume 11B may be treated to control reflection, diffraction or other like phenomena.

The camera(s) 12 may include one or more cameras 12, though a single one is illustrated. For simplicity, the camera will be referred to in the singular though more cameras may be present. The camera 12 may be a high-resolution digital camera or digital cameras (e.g., 3CCD camera), oriented to take global images of the medication items. The expression camera is used generically, but in essence 12 represents an assembly of components to capture images, such components including for example a lens or lenses, a shutter, an aperture, an image sensor (e.g., CMOS, CCD), film, a memory card, combinations thereof, etc. Stated differently, some of the parts of an off-the-shelf camera may not all be present in camera(s) 12.

In an embodiment, the camera 12 faces down in the imaging volume 11B and is positioned above the tray 15 of medication items to take a plan view of the tray 15, and the medication items it supports. The camera 12 may hence produce an image of the tablets. It may be required to lay all tablets manually on the tray 15 or like support surface to ensure that at least a full plan view of each tablet may be obtained. Alternatively, it may be sufficient to obtain an image of a tablet partially obstructed by an adjacent tablet.

Referring to FIGS. 1 to 5, the verification system 10 has a plurality of light sources 13 that serve different purposes. The light sources 13 may be known as lights, flashes, flash head or flash devices (e.g., electronic flash), lighting, etc. The light sources 13 are concurrently referred to with reference number 13, but additional characters may be affixed to 13, to indicate the function and/or location among an array of the light sources 13. Each light source 13 may be independently powered, and may include a light emitting component, such as a flash tube, LED, etc. Moreover, each light source 13 may integrate the light emitting component inside a concave reflector (fill-in reflector), with additional components that may include a light diffusing panel. In an embodiment, the light diffusing panels are rectangular in shape, although other shapes are considered as well. According to an embodiment, LEDs, such as 2835 surface mounted (SMD) LEDs, may be used, as a possibility among others. In an embodiment, the LEDs are 6000K. Other light temperatures are contemplated.

According to an embodiment, a first light source 13 is a contour light source 13A. The contour light source 13A may be located under the tray 15, in the imaging volume 11B. In an embodiment, the contour light source 13A is oriented toward and faces the camera 12. The contour light source 13A may have a light diffusing panel that is larger than the surface of the tray 15 receiving the medication items, for all of the medication items to be in line with the ray of light from the contour light source 13A.

As a consequence, the image captured by the camera 12 through an emission of the contour light source 13A shows the medication items as shadows, whose contour is well contrasted as a consequence of the light source 13A facing the camera 12. The medication items are imaged as umbra when captured by the camera 12 using lighting from light source 13A.

The light sources 13 may also include relief light sources, shown in an array of three light sources 13B1, 13B2 and 13B3. The verification system 10 may have two or more relief light sources 13B. The relief light sources 13B emit light from different points to create shadow with surface features on the medication items, if non continuous surface features are present, such as channels, engraved markings (e.g., characters), decorative features, etc. The relief light sources 13B are operated sequentially, whereby the verification system 10 may obtain as many relief images as there are light sources 13B in the group of relief light sources 13B, or more or fewer. The arrangement of three light sources 13B1, 13B2 and 13B3 covers 180 degrees from a center being on the support surface. Stated differently, relative to the support surface for the medication items, two of the light sources 13B may be on opposite sides. The medication items are lit up sequentially from the different emission points, i.e., 13B1, 13B2 and 13B3, and this may include two or more light sources in the group of 13B.

In order to achieve suitably high contrast to create surface relief, the relief light sources 13B are in relatively close proximity to the receiving surface of the tray 15. In an embodiment, a center of the relief light sources 13B is at a height ranging between 1.38" and 2.38" from the receiving surface of the tray 15, as shown in FIG. 4.

The light sources 13 may also include one or more color light sources 13C. The color light source(s) 13C are provided to highlight the colors (a.k.a., colours) of the medication items. In an embodiment, other ones of the light source may be used to execute the function of the color light sources 13C whereby the latter may be optional. However, it may be desired to have dedicated color light sources 13C, to ensure that zones of shadow may not have an impact on the colors on the capture images. For this reason, in an embodiment, the disposition of color light source 13C may be higher up than the array of relief light sources 13B, as follows. As a reference, a camera axis Y can be defined as being a normal of the plane of the contrast light source 13A passing through the lens of the camera 12. The light sources 13C1 and 13C2 each have a color axis from their respective center, and intersecting the camera axis on the receiving surface of the tray 15. The angles θ are between the color axes and the camera axis, and range between 20° and 30°. In an embodiment, the camera axis defines a symmetry axis for the light source 13C1 and 13C2. Likewise, the camera axis may be a symmetry axis for the array of relief light sources 13B. The light sources 13C1 and 13C2 may be operated simultaneously to obtain a single image for color determination. However, it is contemplated to operate them sequentially, and obtain more than one image.

Figure 4:
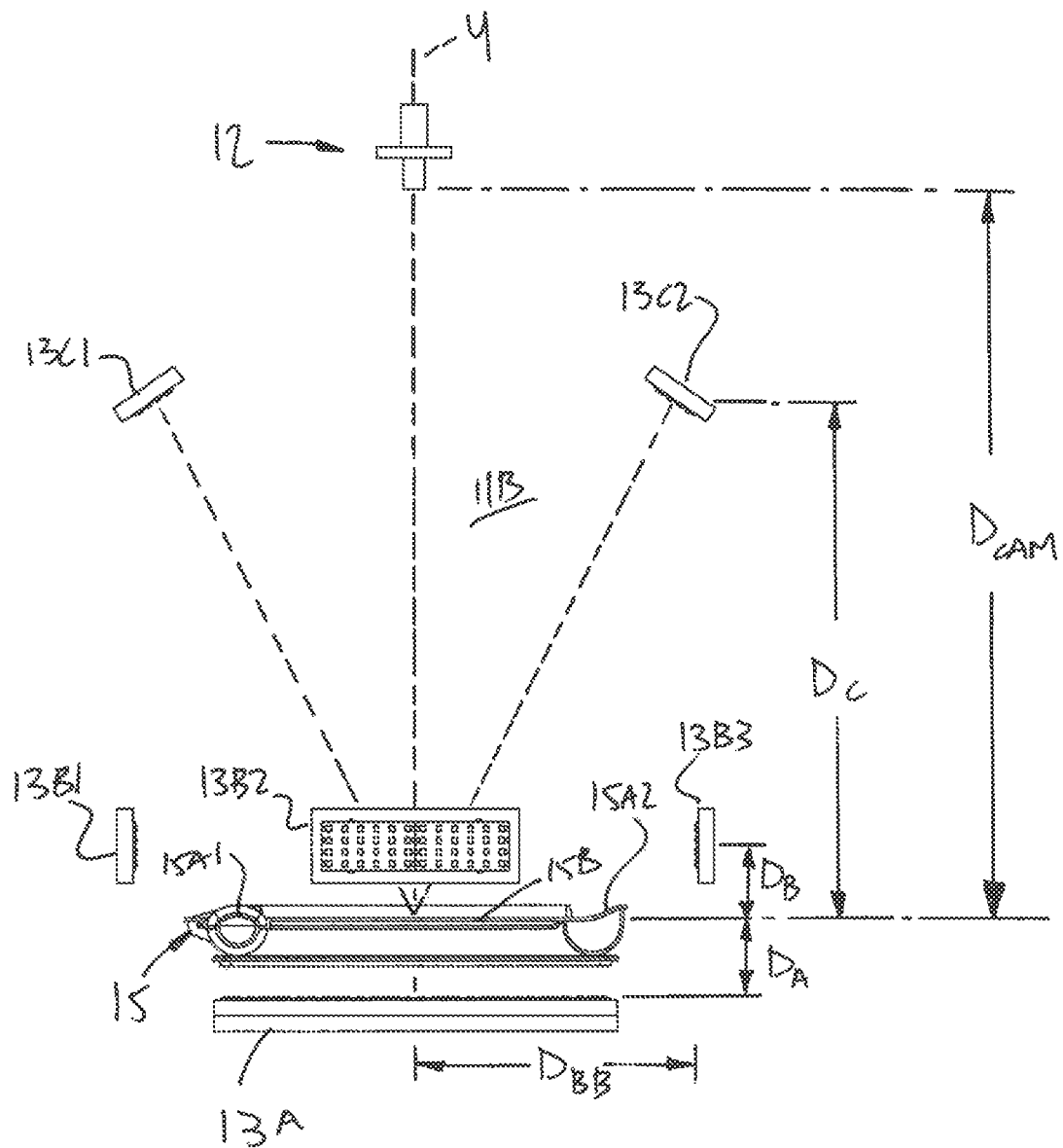
FIG. 4 is an elevation view of the camera, light sources, and tray of the verification system of FIG. 1.

Referring to FIG. 4, an embodiment of dimensions/distances of the camera 12 and light sources 13 is provided as an example. The distance of the light sources 13 are given relative to a support surface of the medication items (e.g., that of the tray 15), as the support surface represents a location plane for the medication items.

In the embodiment, the distances are as follows:

$D_A$ from light source 13A to support plane=1.75 in±1.00 in $D_B$ from center of light source 13B to support plane=1.88 in±0.50 in $D_{BB}$ from light source 13B1 and 13B3 to axis Y=6.58 in±2.00 in with the light source 13B1 and 13B3 equidistantly spaced $D_C$ from light source 13C to support plane=12.67 in±3.00 in $D_{CAM}$ from camera 12 to support plane=18.11 in±6.00 in Therefore, relative to the support plane, the sequence of components in order of height increase is the array of relief light sources 13B, the color light sources 13C, and the camera 12. The camera 12 is centered relative to the support plane via camera axis Y, whereas the light sources 13B and 13C are offset from the camera axis Y. In an embodiment, the normal to a plane of the light sources 13B is transverse to the camera axis Y, with their projections on a vertical plane being for example perpendicular. In an embodiment, the projections of the normals to a plane of the light sources 13C intersect the camera axis Y at the support surface on a vertical plane.

The interface unit 14 may include a screen, as in FIG. 1, such as a touchscreen. The screen 14 may be located in the casing body 11 so as to be above the tray 15. Therefore, from the point of view of a user, both the interface unit 14 and the tray 15 (or equivalent support surface for the medication items) may be simultaneously in the line of sight of the operator.

Referring to FIGS. 1-4, the tray 15 may be removable, and may have a pair of receptacles 15A1 and 15A2 between a transparent or translucent support surface 15B thereof. Both receptacles 15A1 and 15A2 may have a tapering open end, and a trough body. A first of the receptacle, i.e., 15A1, may have a releasable cover, while the other of the receptacles, 15A2, may not. The receptacle 15A1 with such a cover may be used to capture and isolate proper medication items, whereas outlier medication items may be swiped into the open top receptacle 15A2 to be reinserted in a container via the tapering open end, or vice versa. Other configurations are considered. The support surface may even be without the receptacles, or part of a support table or base of the casing body 11.

Figure 5:
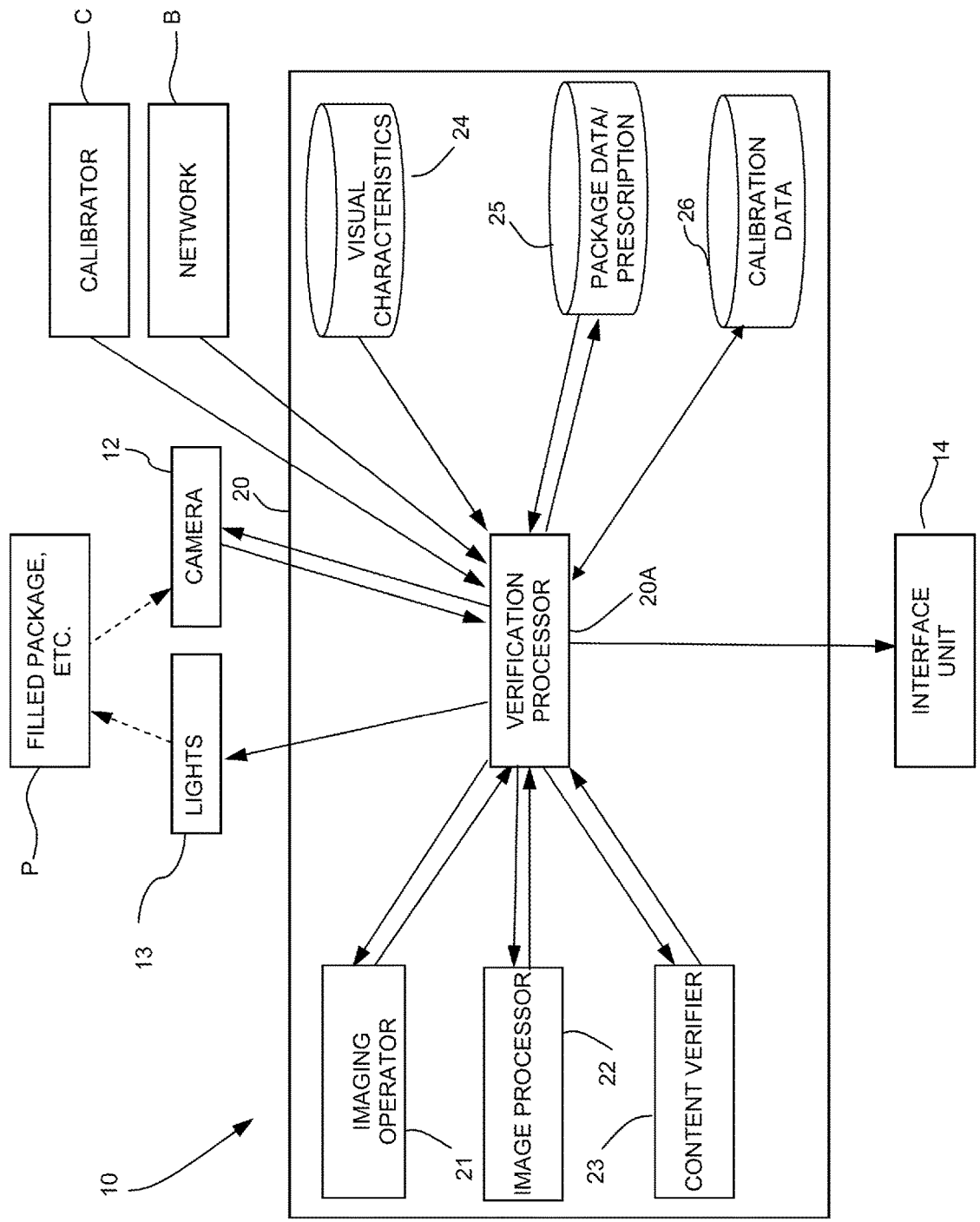
FIG. 5 is block diagram of a verification system for medication packaging in accordance with an embodiment of the present application.

Referring to FIG. 5, the verification unit of the verification system 10 may include a processor or processors, such as verification processor 20A, and non-transitory computer-readable memory communicatively coupled to the processing unit and comprising computer-readable program instructions executable by the processing unit, for instance in the form of modules. The verification unit 20 may drive the camera 12 and light sources 13 to generate and capture the images of the medication items, such as emptied from their medication package A or other container. The verification unit 20 may verify the contents of the package A for outliers, or in comparison with a patient prescription or with a container identifier (e.g., using the DIN), using image processing, to determine if the medication items match the prescription or the container label. The verification unit 20 comprises a verification processor 20A that is typically a processing unit of a computer (PC, laptop, etc) and will run a verification application. It is considered to use an efficient processor (e.g., quad-core processor, among others) to efficiently perform the verification. The verification processor 20A may be enclosed in the casing body 11, or may be located remotely. For example, the verification unit 20 may be a standalone tablet or laptop communicatively connected to the operable components of the verification system 10.

The verification processor 20A operates an imaging operator module 21 in order to capture the various images necessary to perform the requested verifications. The operator module 21 may consequently drive the camera 12 and any set or combination of sets of the light sources 13, as a function of the requested verification. For example, if an operation of pill count is requested, it may suffice to capture images with contour light source 13A. Likewise, if the medication item being verified as a unique peripheral contour, in an embodiment the capture of images illuminated with the contour light source 13A may be sufficient. The imaging operator module 21 may select a lighting scheme as a function of operations requested by the user, and/or as a function of the identification of anticipated medication item, for example.

With the images based on the driving by the imaging operator module 21, the image processor module 22 may define the visual characteristics of the medication items. The visual characteristics may include geometry, shape, color, tint, relief marks and/or surface features, marks, data, symbols, barcode, data matrix, etc. The color may be quantified or provided with an identity by the image processor module 22. The image processor module 22 may use the images captured using the various light sources 13A, 13B and/or 13C as driven by the imaging operator module 21.

A content verifier module 23 verifies the identity of the medication items using the visual characteristics of the images from the image processor module 22. The content verifier module 23 may accesses a visual characteristics database 24, that contains data pertaining to the visual characteristics of pills and tablets. In the visual characteristics database, each medication item has a reference profile, with a full identification (name, reference number, posologic data, DIN), along with an outline, a geometry, a pattern, color data, marking (brand, name, trademark) or a code (e.g., barcode, data matrix, etc). The geometry may consist in a three-dimensional model of the dose, or in a plurality of flat elevation models (e.g., for instance as laid on a flat surface). In the case where the verification system 10 has a single camera 12, the dose reference profile may have outline models of the medication items, also known as doses, for all possible orientations. The reference profile comprises enough information to differentiate doses from one another. Even though the visual characteristics database 24 is shown in the verification unit 20, it may be cloud based, on operator servers, etc. Such embodiments are generically shown as network B. In an embodiment, medicaments each have a dose reference profile as provided by the manufacturer of the medicament, as detailed hereafter. Alternatively, the dose reference profiles may be created by the operator of the verification system 10, or downloaded from an external source B. In creating the images of the dose reference profiles and in verifying medication packages with the system 10, similar lighting and background conditions may be used, as during the imaging, as described with reference to calibrator C below.

The verification processor 20 may also access a package date database and/or prescription database 25. In an embodiment, the prescription database 25 comprises prescription data for a client/patient. The prescription data is an identification of the medication item that is prescribed to the client/patient. The jobs featuring the prescription data may be obtained from a pharmacy network B (i.e., LAN, or remote pharmacy server), may be downloaded from another source, or may be programmed, stored and updated in the verification system 10. The patient file may be identified by the verification processor 20 using any information obtained from the images (e.g., DIN, bar code, data matrix, characters for OCR), or following manual steps of identification by the operator (e.g., scanning, manual entry of patient id) entered via the interface unit 14. The verification processor 20 may therefore comprise a scan reader to read such codes, or may rely on the camera 12 to process such code and identify and obtain the patient prescription.

The package date database 25 may be used to correlate package data label to the content of the container. The prescription data is an identification of the medication item that is prescribed to the client/patient. For instance, the package data may provide the identity of the medication item (e.g., via the DIN), for the verification processor 20A to then obtain the reference profile for the medication item, to be used by the content verifier module 23. The package data and identity may be obtained from the pharmacy network B (i.e., LAN, or remote pharmacy server), may be downloaded from another source, or may be programmed, stored and updated in the verification system 10. Again, the verification processor 20 may therefore comprise a scan reader to read such codes, or may rely on the camera 12 to process such code and identify and obtain the package data.

Therefore, with the medication items imaged, the content verifier module 23 may determine one or more of the following queries: number of medication items in the container; identity of medication items in the container; presence of outliers in the container; conformity between patient prescription and type of medication item and/or number of units; and/or conformity between container identification and medication item. With a bigger tray 15, for instance with an array of receptacles, the verifier module 23 may verify medication dose packs of the type having a grid of receptacles, with each receptacle associated with a different intake period.

In an embodiment, the content verifier module 23 uses the patient data from the patient prescription database 25 to obtain the reference profile of the medication item. Accordingly, instead of performing an identification of an image among a vast number of images, the content verifier module 23 compares the expected reference profiles to the images. Such a comparison may reduce the processing to be performed by the verification processor 20A to verify images, and confirm the identity of the medication items.

The verification processor 20A produces a verification report through the interface unit 14 providing the comparison data. Accordingly, the verification report may be a confirmation that the identity corresponds or not to the patient prescription or to the container label. The verification report may indicate that the count is in excess or in shortage of inventory. The verification report may also be a count of medication items, with the system 10 serving to perform the periodic inventory of medication items. The verification report may also provide some error messages, requiring a visual inspection by the pharmacy attendant in the event that the package image provides insufficient visual data for some medications items, or that some medication items do not match any dose reference model. Considering the risks related to improper prescription, the verification steps performed by the verification system 10, and the verification report must be precise and accurate, and any potential error must be reported to the pharmacy attendant/pharmacist. The interface unit 14 may indicate that some of the medication items are outliers, for instance by a screen pointing to the outliers. A real time video feed may be operated on the screen for a user to navigate the manipulation of the outlier.

The interface unit 14 may be a printer, a monitor, data output (e.g., in the form of a file data for network communication), and/or any other suitable interface. Accordingly, the interface unit 14 outputs the verification report in any appropriate format, such as a printout, a result screen, an email, a file, etc.

An image database may be used to keep the images of each verification performed by the verification processor 20A, with for instance the data related to the verification. The files in the image database may be used for subsequent verification.

The verification system 10 may perform other tasks related to identifying the filled medication package A. For instance, the imaging unit 11 may obtain patient data from the medication package A. For instance, the imaging unit 11 may have a bar code reader, and the medication package A may have a bar code representing the patient. The verification unit 12 may thus automatically obtain the patient prescription from the database 22 if the patient is identified with the imaging unit 11. Also, the verification system 10 may be used to quantify the amount of a same dose in a package, as described briefly above when enumerating the various packages A with which the verification system 10 may be used.

In order to contribute to the correspondence between the images obtained by the verification processor 20A and the those from the various database, a calibrator C and/or calibration data 26 may be available (the calibration data 26 obtained for instance from network B or being programmed in the verification unit 20). In an embodiment, the calibrator C is a color card(s) that is imaged by the verification unit 20, for example as illuminated by the lights 13C. The color card(s) has a predetermined known color therein, whose parameters are precisely known. Therefore, the verification unit 20 may quantify the variation between the imaged color of the calibrator C with programmed visual characteristics. This may for instance allow the verification unit 20 to seek images from database 24 at given levels of tint or contrast, and/or to factor in the variation to properly identify the visual characteristics of the medication items. As another possibility, the driving of the light sources 13 is adjusted, for the wavelength of the light produced by the light source 13 to be controlled to ensure that the correct color is reflected back to the digital camera of the camera 12. The wavelength used by the light sources 13 may replicate the wavelength used to image profile pictures of medication items. In an embodiment, the calibrator C is only performed at a set-up stage and/or at periodic maintenance.

Therefore, the image of the medication item defines at least a partial outline of the medication item, preferably as naturally lying on a flat surface, but alternatively in any given orientation, in addition to the color (e.g., tint and contrast). The image may also contain ornamentation of the tablet, such as a brand name. The image of the tablet may also comprise an image of a barcode on the tablet. For instance, some tablets may have on their surface a data matrix (a.k.a., two-dimensional matrix barcode), which data matrix represents full tablet information. Other types of coding may be used as well.

Figure 6:
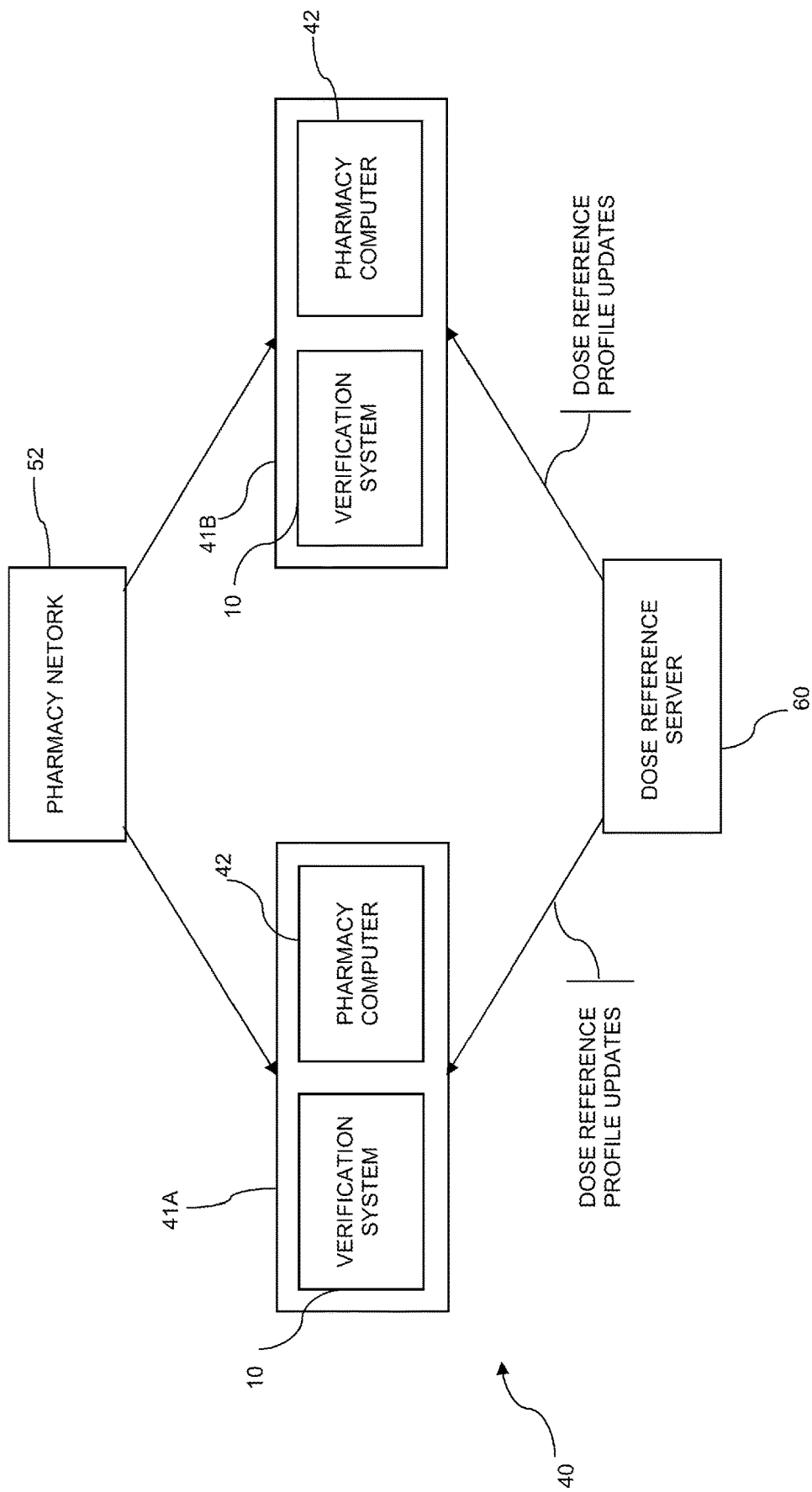
FIG. 6 is a block diagram of verification systems of FIG. 1, in conjunction with a pharmacy network.

Referring to FIG. 6, there is illustrated at 40 a network arrangement for multiple verification systems 10. In FIG. 6, the verification systems 10 are shown as being present in two pharmacies, namely 41A and 41B, although numerous other verification systems may be present in other pharmacies in the same network.

Each pharmacy has in addition to the verification system 10 a pharmacy computer 42, that performs the usual tasks related to prescriptions and pharmacy management: e.g. maintaining and updating patient profiles, managing inventory, etc. The verification system 10 and the pharmacy computer 42 may be share a single processor or may be two separate units. If the verification system 10 and the pharmacy computer 42 are a single processor, the verification unit 20 may be part of a software performing the aforementioned features.

The pharmacy computers 42 are connected to a pharmacy network 50. For instance, the pharmacy network 50 may keep patient prescription profiles, provide medication updates, etc.

The verification systems 10 are connected to a dose reference server 60 in a client-server model, and may for instance be a proprietary server, cloud-based, etc. The dose reference server 60 is used to maintain a master of reference profiles. Therefore, the dose reference server 60 is operated to store updated visual parameters for medication items, for instance in visual format, as well as all relevant information related to the medication (e.g. bar codes, data matrix, new formats, new doses). The dose reference server 60 provides updates to the verification systems 10, in the form of updated or new reference profiles, additional or updated information for existing profiles, etc.

The visual characteristics database 24 of the verification systems 10 (FIG. 5) may thus be continuously updated with the profiles from the dose reference server 60. According to another embodiment, the verification systems 10 obtain dose reference profiles on a per-verification basis. For instance, a verification system 10 may download specific reference profiles upon identifying the expected medication of a patient prescription profile, for subsequent verification. The dose reference server 60 may also or alternatively provide the relevant information to or through the pharmacy computer 42.

Figure 7:
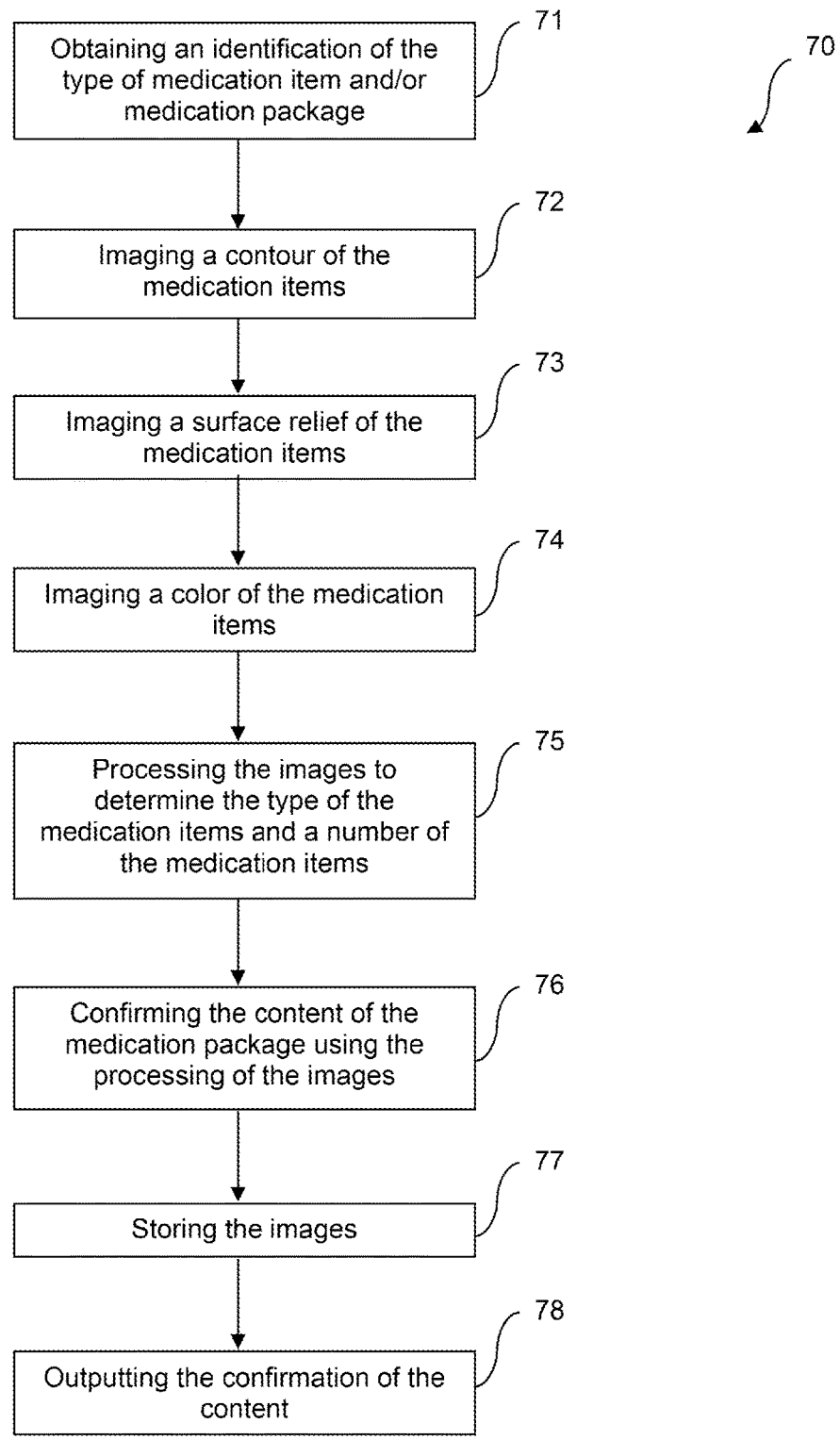
FIG. 7 is a flow chart of a method for verifying the contents of a medication packaging in accordance with another embodiment of the present disclosure.

Referring to FIG. 7, there is illustrated a method 70 for verifying medication content in a medication package.

The method 70 may be performed using the verification system 10 for some steps.

According to 71, an identification of the type of medication item and/or medication package and/or patient prescription is obtained. This may be performed in different ways. For example, a data file may be received, a manual entry may be received, a scan of a label may be performed, with subsequent information retrieval and/or scan analysis, character recognition, etc. In an embodiment, 71 entails obtaining/identifying a patient prescription first, and subsequently obtaining an identification of the type of medication item and/or medication package, to ensure a correspondence between the medication items in the patient prescription, and the medication container then selected by an operator in a response to the patient prescription.

According to 72, with the contents of the medication package emptied on the tray 15 or equivalent, or with a dose pack on the tray 15, a contour of the medication items is imaged. This may be performed by operating the contour light source 13A.

According to 73, a surface relief of the medication items is imaged. In an embodiment, the array of light sources 13B is used therefor. The light sources 13B may be operated sequentially to obtain one or more images by light source 13B. This may not be done in an embodiment, for example in a scenario in which the medication items are of the type without embossing, or with printed information thereon.

According to 74, a color of the medication items may be imaged, for instance using the color light sources 13C. In an embodiment, a calibration is performed beforehand, for instance using a calibrator color. Step 74 may entail imaging with lighting from the light sources 13C packages for ointments or creams. This may be performed to store an image of a prescription, to keep a history of a patient file, for traceability.

The imaging may entail performing one or more of 72, 73, and/or 74, in any particular order. In an embodiment, the method 70 only performs one of 72, 73, 74 as it may suffice in performing a subsequent confirmation.

According to 75, the images are processed to determine the type of the medication items and/or a number of the medication items.

According to 76, a confirmation of the content of the medication package is made using the processing of the images. This may include one or more of: identifying that the medication items do or do not match the label on the medication package, and/or the medication items do not match a patient prescription, and/or there are outliers, among other things.

According to 77, optionally, the images are stored, for instance in a patient file.

According to 78, the confirmation of the content is output. The output may occur in real-time, for instance by a display of the outliers.

The invention claimed is:

1. A system for verifying medication doses in a filled medication package, comprising
 a processing unit; and a non-transitory computer-readable memory communicatively coupled to the processing unit and comprising computer-readable program instructions executable by the processing unit for:

obtaining an identification of a type of medication item and/or medication package containing the medication item, imaging a contour of the medication items by operating at least a first light source while the medication items are emptied from the filled medication package onto a single flat support surface of a tray, imaging a surface relief of the medication items by operating a first set of lights differing from the first light source, processing the images, confirming the content of the medication package relative to identification of a type of medication item and/or medication package using the processing of the images, and outputting the confirmation of the content for subsequently reinserting the medication items in the filled medication package.

2. The system according to claim 1, wherein obtaining the identification includes scanning a label on the medication item and determining the identification using the scanning of the label.

3. The system according to claim 1, wherein imaging a contour of the medication items includes operating the first light source from an underside of a surface supporting the medication items to create an umbra effect.

4. The system according to claim 1, wherein imaging the surface relief of the medication items includes by operating sequentially at least a first relief light source and a second relief light source.

5. The system according to claim 4, wherein operating the first relief light source and the second relief light source includes emitting light from opposite sides of a surface supporting the medication items.

6. The system according to claim 5, wherein operating sequentially at least a first relief light source and a second relief light source includes operating a third relief light source between the first relief light source and the second relief light source.

7. The system according to claim 1, wherein operating a first set of lights differing from the first light source includes emitting light from a height of 1.88 in ±0.50 in relative to a surface supporting the medication items.

8. The system according to claim 1, wherein the computer-readable program instructions are for imaging a color of the medication items by operating a second set of lights differing from the first set of lights and from the first light source.

9. The system according to claim 8, wherein operating the second set of lights includes operating the second set of lights from higher than the operating of the first set of light.

10. The system according to claim 8, wherein operating the second set of lights includes emitting light from light-emitting diodes at a temperature of 6000K.

11. The system according to claim 8, wherein the computer-readable program instructions are for calibrating subsequent imaging by initially imaging a known color and processing the known color.

12. The system according to claim 1, wherein the computer-readable program instructions are for storing the images.

13. The system according to claim 1, wherein confirming the content of the medication package includes providing a count of the medication items.

14. The system according to claim 1, wherein confirming the content of the medication package includes identifying at least one outlier.

15. The system according to claim 14, wherein outputting the confirmation of the content includes visually identifying on a display screen an identity of the at least one outlier.

16. The system according to claim 1, further comprising receiving the medication items laid on the single flat support surface of the system prior to imaging the contour of the medication items.

17. A system for verifying medication doses in a filled medication package, comprising
at least one camera;
at least one contour light source;
a set of relief light sources;
a tray defining a single flat support surface configured to support medication items directly laid thereon for imaging, the at least one contour light source and the at least one camera are on opposite sides of the support surface;
a verification unit including a processing unit and a non-transitory computer-readable memory communicatively coupled to the processing unit and comprising computer-readable program instructions executable by the processing unit for
obtaining an identification of a type of medication item and/or medication package containing the medication item,
imaging a contour of the medication items by operating the at least one contour light source while the medication items are emptied from the filled medication package onto the single flat support surface of the tray,
imaging a surface relief of the medication items by operating the set of relief light source differing from the contour light source,
processing the images,
confirming the content of the medication package relative to identification of a type of medication item and/or medication package using the processing of the images for subsequently reinserting the medication items in the filled medication package; and
an interface for producing a verification output based on the confirmation by the verification unit.

18. The system according to claim 17, wherein the verification unit obtains the identification includes scanning a label on the medication item and determining the identification using the scanning of the label.

19. The system according to claim 17, wherein the tray has at least one receptacle on a side thereof, a bottom of the receptacle being lower than the flat support surface.

20. The system according to claim 17, wherein the set of relief light sources includes at least two relief light sources located on opposite sides of a surface supporting the medication items.

21. The system according to claim 17, further including a set of color light sources differing from the set of relief light sources and from the first light source.

* * * * *